United States Patent
Alexander et al.

(10) Patent No.: US 12,230,161 B2
(45) Date of Patent: *Feb. 18, 2025

(54) MODIFIED ANIMAL ORGANS FOR USE IN SURGICAL SIMULATORS

(71) Applicant: INTUITIVE SURGICAL OPERATIONS, INC., Sunnyvale, CA (US)

(72) Inventors: John Alexander, Pinehurst, NC (US); W. Andrew Grubbs, Hillsborough, NC (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/504,223

(22) Filed: Nov. 8, 2023

(65) Prior Publication Data
US 2024/0078931 A1 Mar. 7, 2024

Related U.S. Application Data

(63) Continuation of application No. 16/645,615, filed as application No. PCT/US2017/050491 on Sep. 7, 2017, now Pat. No. 11,847,932.

(51) Int. Cl.
*G09B 23/30* (2006.01)
*A61B 34/00* (2016.01)
(Continued)

(52) U.S. Cl.
CPC ............. *G09B 23/30* (2013.01); *A61B 34/10* (2016.02); *A61B 34/30* (2016.02); *A61B 34/70* (2016.02);
(Continued)

(58) Field of Classification Search
CPC ....... G09B 23/28; G09B 23/30; G09B 23/306
See application file for complete search history.

(56) References Cited

U.S. PATENT DOCUMENTS

| 5,320,537 A | 6/1994 | Watson |
| 5,410,016 A | 4/1995 | Hubbell et al. |

(Continued)

FOREIGN PATENT DOCUMENTS

| RU | 2223787 | 2/2004 |
| WO | 9629370 | 9/1996 |

(Continued)

OTHER PUBLICATIONS

Vertut, J., and Coiffet, P., "Robot Technology: Teleoperation and Robotics Evolution and Development," English translation, Prentice-Hall. Inc., Inglewood Cliffs, NJ, USA 1986, vol. 3A, 332 pages.

(Continued)

*Primary Examiner* — Kurt Fernstrom
(74) *Attorney, Agent, or Firm* — ALLEN, DYER, DOPPELT, + GILCHRIST, P.A. Attorneys at Law

(57) ABSTRACT

Modified animal tissues, organs, and organ systems for use in simulated surgical procedures are disclosed. The tissues, organs, and/or organ systems can be modified by enhancing their electrical conductivity, by including simulated contents mimicking what would normally be present in live animals, and by having fake blood perfusing through them. Portions of different tissues, organs, or organ systems, which can be from the same or different animals, can be adhered to provide hybrid/chimeric tissues, organs, or organ systems, and also used for simulated surgical procedures. These modifications can provide surgeons with a more realistic experience during a simulated surgical procedure.

23 Claims, 5 Drawing Sheets

(51) Int. Cl.
*A61B 34/10* (2016.01)
*A61B 34/30* (2016.01)
*G06T 19/00* (2011.01)
*G09B 23/28* (2006.01)

(52) U.S. Cl.
CPC .......... *G06T 19/006* (2013.01); *G09B 23/285* (2013.01); *G06T 2210/41* (2013.01)

(56) References Cited

U.S. PATENT DOCUMENTS

| | | |
|---|---|---|
| 5,582,596 A | 12/1996 | Fukunaga et al. |
| 5,643,551 A | 7/1997 | Namikawa et al. |
| 5,665,067 A | 9/1997 | Linder et al. |
| 5,749,968 A | 5/1998 | Melanson et al. |
| 5,792,135 A | 8/1998 | Madhani et al. |
| 5,800,538 A | 9/1998 | Slepian et al. |
| 5,817,084 A | 10/1998 | Jensen |
| 5,874,500 A | 2/1999 | Rhee et al. |
| 6,051,248 A | 4/2000 | Sawhney et al. |
| 6,121,341 A | 9/2000 | Sawhney et al. |
| 6,217,894 B1 | 4/2001 | Sawhney et al. |
| 6,331,181 B1 | 12/2001 | Tierney et al. |
| 6,352,710 B2 | 3/2002 | Sawhney et al. |
| 6,387,977 B1 | 5/2002 | Sawhney et al. |
| 6,441,577 B2 | 8/2002 | Blumenkranz et al. |
| 6,491,701 B2 | 12/2002 | Tierney et al. |
| 6,817,974 B2 | 11/2004 | Cooper et al. |
| 7,544,062 B1 | 6/2009 | Hauschild et al. |
| 7,963,913 B2 | 6/2011 | Devengenzo et al. |
| 2002/0100065 A1 | 7/2002 | Zanjani |
| 2009/0017438 A1 | 1/2009 | Roy et al. |
| 2011/0143331 A1 | 6/2011 | Roy et al. |
| 2013/0177890 A1 | 7/2013 | Sakezles |
| 2013/0330700 A1 | 12/2013 | Feins et al. |
| 2014/0302475 A1 | 10/2014 | Sakezles |
| 2016/0314717 A1 | 10/2016 | Grubbs |
| 2016/0329000 A1 | 11/2016 | Feins et al. |
| 2017/0022348 A1 | 1/2017 | Iwata et al. |
| 2017/0186340 A1 | 6/2017 | Ogawa et al. |
| 2018/0144662 A1 | 5/2018 | Tassone et al. |
| 2020/0005679 A1 | 1/2020 | Grubbs et al. |
| 2020/0286406 A1 | 9/2020 | Alexander et al. |

FOREIGN PATENT DOCUMENTS

| | | |
|---|---|---|
| WO | 9934833 | 7/1999 |
| WO | 0015117 | 3/2000 |
| WO | 02051383 | 7/2002 |
| WO | 2010027613 | 3/2010 |
| WO | 2014134597 | 9/2014 |
| WO | 2016122923 | 8/2016 |

OTHER PUBLICATIONS

Marques et al. "Simulated Biological Fluids With Possible Application in Dissolution Testing", Aug. 2011, pp. 1-14. See Priority U.S. Appl. No. 16/645,615, filed Mar. 9, 2020.

Cherniy V.I. i dr. «Ratsionalnaya infuzionnaya terapiya», Donetsk. Izdatelskiydom «Zaslavskiy», 2012, pp. 14-22, 31-34,50, 62, 121, 166-176. (Translation Not Available) See Priority U.S. Appl. No. 16/645,615, filed Mar. 9, 2020.

"Kak sdelat iskusstvennuyu krov", Retrieved from the Internet: URL: http://anydaylife.com/post/1766, Oct. 2013, pp. 1-5. (Translation Not Available) See Priority U.S. Appl. No. 16/645,615, filed Mar. 9, 2020.

Prigotovleniye inyektsionnykh i infuzionnykh rastvorov», Retrieved from the Internet: URL: https://medin, Dec. 2016, pp. 1, 2, 5, 6, 8. (Translation Not Available) See Priority U.S. Appl. No. 16/645,615, filed Mar. 9, 2020.

Extended European Search Report for Application No. EP17924529.5 mailed on Feb. 18, 2021, 7 pages. See Priority U.S. Appl. No. 16/645,615, filed Mar. 9, 2020.

International Preliminary Report on Patentability for Application No. PCT/US2017/050491, mailed on Mar. 19, 2020, 8 pages. See Priority U.S. Appl. No. 16/645,615, filed Mar. 9, 2020.

International Search Report and Written Opinion for Application No. PCT/US2017/050491, mailed Jun. 21, 2018, 9 pages. See Priority U.S. Appl. No. 16/645,615, filed Mar. 9, 2020.

MODIFIED ANIMAL ORGANS FOR USE IN SURGICAL SIMULATORS

CROSS-REFERENCE TO PRIORITY APPLICATIONS

This application is a continuation application of U.S. patent application Ser. No. 16/645,615 filed Mar. 9, 2020, which is based on a 371 Application as PCT/US2017/050491 filed Sep. 7, 2017, the disclosures which are incorporated herein by reference in their entirety.

FIELD OF THE INVENTION

The present invention relates to the field of surgery, where the surgery is performed on a surgical simulator rather than on a live human or animal. The invention further relates to tissue, organs, and organ blocks for use in surgical simulators.

BACKGROUND

Historically, surgery has been performed by making relatively large incisions in a patient to access a surgical site. More recently, robotic surgery allows a surgeon to perform procedures through relatively small incisions. The surgeon passes an endo scope through a small incision, and the endoscope includes a camera that allows the surgeon to view the patient's internal organs. Robotic procedures tend to be less traumatic, and to have shorter recovery times, than conventional surgical procedures.

Representative examples of procedures that can be performed using robotic surgery include heart surgery, lung surgery, prostate surgery, hysterectomies, joint surgery, and back surgery. Companies like Intuitive Surgical, Inc. ("Intuitive") provide robotic systems that allows surgeons to perform minimally invasive surgery, including coronary artery by-pass grafting (CABG) procedures. The procedures are performed with instruments that are inserted through small incisions in the patient's chest, and controlled by robotic arms. The surgeon controls the movement of the arms, and actuates "effectors" at the end of the arms using handles and foot pedals, which are typically coupled to electronic controllers. Recent advances allow the surgeon to use voice commands, or "line-of-sight," to control the movement of the endoscope and other robotic arms. Further, the surgeon can "feel" the force applied to the tissue, so as to better control the robotic arms.

In addition to using an endoscope to view the surgical site, the surgeon can use a laser or scalpel to cut tissue, an electrocautery device to cauterize tissue, a "grabber" to grab tissue, such as cancerous tissue, to be removed from the body, and lights to illuminate the surgical site.

Each instrument has a unique control interface for its operation, so a surgeon, or pair of surgeons, must independently operate each device. For example, a surgeon might use a first foot pedal to control an electrocautery device, a second foot pedal to operate a robotic arm, and another interface to operate a laser. The handles and a screen are typically integrated into a console operated by the surgeon to control the various robotic arms and medical instruments.

It typically requires a certain amount of time to train surgeons to use these robotic systems. Training has historically involved human cadavers. More recently, a company called Kindheart has adapted organs derived from dead animals, including heart, lungs, and the like, with tubing, pumps, switches, and the like, to mimic the action of living organs. For example, a heart can pump with heartbeats set to motion by a pump so that the heart rate is adjustable and controllable, and lungs can inflate and deflate on command.

There are some limitations associated with using these organs. One set of limitations relates to the blood pumped through the organs. Theater blood commonly includes detergents, which can cause the blood to foam, the osmolarity of theater blood is typically lower than regular blood, causing organs to swell, and theater blood lacks components which allow the blood to clot. Another set of limitations relates to the normal contents of the organs. For example, when performing surgery on the bowel, the osmolarity of the contents of the bowel is typically insufficient to allow one to perform electrocautery.

Accordingly, it would be useful to have animal tissues, organs, or organ systems which a perfused with a fake blood composition, and/or include contents which allow the surgeon to perform electrocautery. The present invention provides such tissues, organs, and organ systems.

SUMMARY OF THE INVENTION

In one embodiment, the invention relates to modified animal tissues, organs, and organ systems for use in simulated surgical procedures. The tissues, organs, and organ systems include components which allow them to be used in simulated surgical procedures, particularly where electrocautery is used.

In one aspect of this embodiment, the tissues, organs, and/or organ systems are modified using "chemical enhancements" to make them work better with surgical tools (robotic, laparoscopic and conventional), such as by enhancing their electrical conductivity by filling or partially filling them with salt solutions. As used herein, the term "partially filled" means between about 10 and about 99% of the volume of the tissue, organ, or organ system. One example of a suitable salt solution is a solution of salt, such as sodium chloride or potassium chloride, in a hydrogel formulation, such as KY jelly, polyethylene glycol, and the like. The use of hydrogels can be preferred over ordinary salt solutions because of the added viscosity. The added viscosity tends to add a more realistic "feel" to the tissue, organs, or organ systems.

The animal organs can be modified to include simulated contents that mimic what would normally be present if the animal were alive. For example, organs in the gastrointestinal tract, such as a stomach, duodenum, cecum, upper or lower intestine, or colon, ordinarily might include undigested food. The gall bladder includes bile, and the spleen includes a significant blood supply. The brain includes cerebrospinal fluid, the lymphatic system includes lymphatic fluid, and the abdomen includes abdominal fluid. When cut, the organs may exude these fluids, as well as odorous chemicals, particularly when the colon is cut. All of these can be mimicked, so as to provide the surgeon with a more realistic experience during a simulated surgical procedure.

For example, a colon can be filled or partially filled with a hydrogel formulation, such as KY jelly (which includes water, glycerin, hydroxyethylcelluose, chlorhexidine gluconate, gluconolactone, methylparaben, and sodium hydroxide), and a salt, such as sodium chloride, at concentrations sufficient for electrocautery to be performed. Food, such as peas and carrots, can be present, as can pudding (for example, chocolate pudding can provide the color of fecal matter) and other foodstuffs.

Odorants, such as butyric acid (one of the odorous components of feces) can also be present, ideally at concentrations which are not particularly noticeable until the colon has been cut, but which are noticeable when the colon has been cut. Successful electrocautery can be determined, for example, by the lack of continued leakage of the liquid/solid components present in the colon, and also by the lack of odor (resulting from the lack of continued leakage of the odorant(s)).

Another way to simulate a tissue, organ, or organ system in need of electrocautery is to modify the tissue, organ, or organ system to include a source of fake blood perfusing through it, and components which mimic what is normally found in an organ/organ system that would leak out if the organ were penetrated. The surgeon can then practice how to deal with an emergency situation, such as a bleed, or leakage of fluid from a punctured/penetrated organ using electrocautery techniques.

For example, to simulate colonic surgery, an animal colon can be modified to include a tube attached to a vein or artery, so as to be able to perfuse "blood" through the colon, and the colon can include simulated undigested, partially digested, and/or digested food.

Accordingly, in another aspect of this embodiment, the tissues, organs, and/or organ systems are modified by attaching tubing to one or more veins or arteries, which tubing ideally has a quick-connect port or valve, such that "blood" can be perfused throughout the organ. The blood ideally has sufficient salt concentration that the perfused tissue, organ, or organ system can be subjected to electrocautery conditions.

Although animal blood can be used, it can be desirable to use a "fake" blood composition. The fake blood composition includes one or more colorants, including dyes and inks, which preferably color the composition red, but which can be any desired color. Examples of such colorants include, but are not limited to, food dyes such as red dye #40 and FD&C blue #1. Although red dyes can be used exclusively, blue or green dyes can be used to achieve a more realistic shade. As a general rule, arterial blood is bright red, while venous blood is a dark maroon color.

The fake blood composition further includes one or more salts, including sodium and potassium chloride, and buffers such as those including phosphate, ascorbate, acetate, and similar salts, and their conjugate acids. For example, standard 0.9% phosphate buffered saline can be used.

The amount of salts should be selected to provide a fake blood composition with a sufficient ionic concentration that the tissues, organs, or organ blocks through which it is perfused can be cauterized using electro-cautery techniques. The osmolality and osmolarity are typically within about 20% of that of human blood. Blood osmolality is typically measured in milliosmoles per kilogram, and a normal result is typically between about 275 and about 303 milliosmoles per kilogram. Accordingly, the fake blood described herein preferably has an osmolality between about 220 and about 400 milliosmoles per kilogram.

The pH of the fake blood composition is preferably within one pH unit of the normal blood pH, which is around a pH of 7.4. Preservatives can also be present, in an amount sufficient to extend the useful shelf life of the composition.

The fake blood compositions can be provided as liquid solutions or dispersions. Because of the protein content, the compositions can quickly degrade if not stored in an aseptic manner. The compositions can be cold filtered (a process known as microfiltration, or MF), for example, through a filter of a suitable size (for example, around a 0.2 micron or 0.5 micron filter) to filter out bacteria, and/or can be pasteurized. The components of the fake blood can also be provided in powder form, for later reconstitution before use.

In use, the blood is perfused through the arteries, veins, and/or capillary beds of animal tissue, organs, or organ blocks during simulated surgical procedures.

Where these types of pre-treated tissues, organs or organ systems are used, they can be supplied in kit form, where they can include components intended to simulate the contents of the organs that might be found during normal surgical procedures, and can be modified to include tubing attached to one or more arteries or veins, and supplied with the artificial blood described herein.

The blood compositions can be supplied, for example, in IV bags or other suitable containers. The bags or containers can be attached to suitable tubing, which can be attached to suitable pumps and/or valves, which can be used to perfuse the blood through the animal tissue, organs, or organ systems.

In other embodiments, portions of different tissues/organs/organ systems, which can be from the same or different animals, can be adhered to provide hybrid/chimeric tissues, organs, or organ systems, and used for simulated surgical procedures. For example, a layer of pig fat can be adhered to organs, such as those found in the gastrointestinal tract, the liver, the spleen, or the gall bladder, so as to simulated an overweight or obese patient. An animal placenta, turned inside out, can mimic the vasculature in tumors, and portions of the "inside out" placenta can be wrapped around tissues, organs, organ systems, veins, arteries, or a spinal cord, to provide a simulated tumor that a surgeon can remove in a simulated surgical procedure. One example of a chimeric organ would be one where a portion of a pig placenta is wrapped around a dog prostate gland, which can optionally, in turn, be placed inside a simulated rectum or a rectum of an animal such as a pig.

In addition to using an inverted placenta to mimic tumors, actual animal tumors can be inserted into a desired tissue, organ, or organ system by making an incision, inserting the tumor, and sealing the tissue/organ/organ system, for example, using surgical glue, caulk, such as silicon caulk, and/or mechanical fasteners such as sutures and/or staples.

Other disease states can be mimicked by modifying the organs to include other abnormalities. Representative abnormalities include blood clots, bleeders, and vascular occlusions.

The tissues, organs and organ systems described herein can be part of a robotic simulated surgical system.

Aspects of the teachings contained within this disclosure are addressed in the claims submitted with this application upon filing. Rather than adding redundant restatements of the contents of the claims, these claims should be considered incorporated by reference into this summary.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provided below as one of skill in the art will recognize that inventive concepts illustrated in various examples can be combined together in order to address a specific application.

Other systems, methods, features and advantages of the disclosed teachings will be or will become apparent to one with skill in the art upon examination of the following figures and detailed description. It is intended that all such additional systems, methods, features and advantages be included within the scope of and be protected by the accompanying claims.

DETAILED DESCRIPTION

Figure 1:
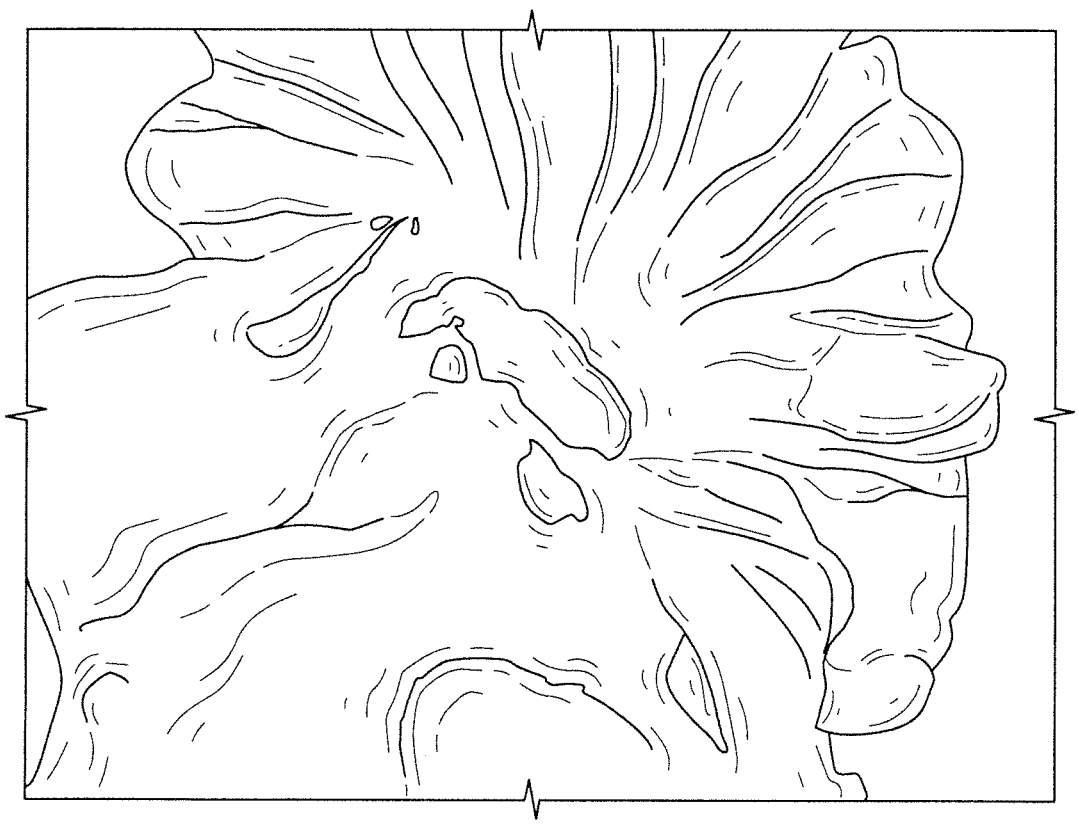
FIG. 1 is a photograph showing a porcine small bowel, including the mesenteric lymph nodes, perpendicular vessel and small bowel.

In the following detailed description, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

In one embodiment, the invention described herein relates to tissues, organs, and/or organ systems which have been modified for use in simulating surgical procedures, including robotic surgical procedures. Examples of simulated surgical procedures include surgery on the bowel or other portions of the gastrointestinal tract, splenectomy, gall bladder removal, appendectomies, spinal surgery, brain surgery, heart by-pass operations, valve replacements or repair, lung re-sectioning, tumor removal, prostatectomy, appendectomy, hernia operations, stomach stapling/lap band operations, orthopedic surgery, such as rotator cuff repair and arthroscopic knee surgery.

In addition to actual operations, the tissues, organs, and organ systems described herein can allow a surgeon to practice electrocautery. Each of these surgeries and/or skill sets can be practiced using an appropriate tissue, organ or organ block, as discussed in detail below.

The systems include one or more surgical simulator units that include animal tissues, organs, or organ systems, providing a non-living but realistic platform on which to perform surgery. The systems also include one or more instruments for performing robotic surgery, so that one or more simulated surgical procedures can be performed on tissues, organs, or organ systems in the surgical simulator units. The systems optionally, but preferably, also include a telecommunications system which allows remote access to, and control of, the instruments used to perform robotic surgery, thus allowing simulated robotic surgery to be performed remotely.

The types of tissues, organs, and organ systems, ways they can be modified to allow electrocautery, and simulated surgical procedures surgery, are described in detail below.

I. Electrocauterization

As used herein, electrocauterization is the process of destroying tissue (or cutting through soft tissue) using heat conduction from a metal probe heated by electric current. The procedure stops bleeding from small vessels (larger vessels being ligated). Electrocautery applies high frequency alternating current by a unipolar or bipolar method. It can be a continuous waveform to cut tissue, or intermittent to coagulate tissue.

In unipolar cauterization, the physician contacts the tissue with a single small electrode. The circuit's exit point is a large surface area, such as the buttocks, to prevent electrical burns. The amount of heat generated depends on size of contact area, power setting or frequency of current, duration of application, and waveform. Constant waveform generates more heat than intermittent. Frequency used in cutting the tissue is higher than in coagulation mode.

Bipolar electrocautery passes the current between two tips of a forceps-like tool. It has the advantage of not disturbing other electrical body rhythms (such as the heart) and also coagulates tissue by pressure. Lateral thermal injury is greater in unipolar than bipolar devices.

Ultrasonic coagulation and ablation systems are also available.

II. Tissues/Organs/Organ Systems

The tissues, organs, and organ systems described herein can be used in simulated surgical procedures, including, but not limited, to those performed using robotics, laparoscopic procedures, and conventional procedures.

Hybrid/Chimeric Organs

In some embodiments, it is not possible to mimic a desired human tissue, organ, or organ system with an animal tissue, organ, or organ system, but it is possible to mimic the tissue, organ, or organ system by combining portions of various animal tissues, organs, or organ systems. The animal tissues, organs, or organ systems can be from the same type of animal, or can be from different animals (i.e., chimeric simulated tissues, organs, or organ systems). The portions of tissues, organs, or organ systems can be adhered together, for example, using surgical adhesives, or caulk, such as silicone caulk. Mechanical means, such as stitches, staples, and the like, can also be used.

In this embodiment, and other embodiments described herein, it can also be possible to use a combination of a dye and an amine, in combination with an appropriate light source, to generate a radical, which can be used to crosslink a gel that includes photoreactive groups, such as acrylate groups. For example, a polyethylene glycol with acrylate groups on its ends can be used. Where one portion of the tissue/organ/organ system to be adhered is painted with the dye, and a solution of the gel is then applied to the other portion of the tissue/organ/organ system to be adhered, the gel can be made to crosslink at the interface between the two portions. The adhesion can be stronger than when caulk is used, as the crosslinking occurs at the interface between the two tissues/organs/organ systems.

Chemistry of this type is described, for example, in U.S. Pat. Nos. 5,410,016, 5,582,596, 5,665,067, 5,749,968, 5,800,538, 5,749,968, 5,874,500, 5,582,596, 6,121,341, 6,387,977, 6,352,710, 6,217,894 6,051,248, and International Patent Publication Nos. WO 96/29370, WO 99/34833, WO 02/51383, and WO 00/15117.

Any suitable biocompatible material can be selected, such as those described in any of the above-identified patents or international patent publications incorporated by reference. Where a two-component liquid tissue coating is used, in one embodiment, the first biocompatible material is a "primer" or "photoinitiator" and the second biocompatible material is a "sealant". As used herein, "primer" is a material that can improve adhesion of another material, or can assist in changing the form of another material in some way. For example, a "photoinitiator" is a material reactive upon exposure to electromagnetic radiation, such as visible light, to cause another material to begin to polymerize or to enhance polymerization of another material. Thus, a photoinitiator can be applied to a surface followed by application of a polymerizable material over the photoinitiator. Exposure of this arrangement to electromagnetic radiation matched for activation with the photoinitiator can cause polymerization of the polymerizable material beginning at the surface and extending away from the surface. As such, adhesion to the surface can be enhanced, and the thickness of the resulting polymer layer on the surface can be controlled by control of the time during which the material is exposed to the radiation. Since the material polymerizes in a direction away from the surface, and may be photoactively-driven depending upon selection of material, when the radiation source is removed, polymerization ends and excess material can be washed away leaving a medically-acceptable coating of material at a predetermined thickness. One preferred material is a "primer" and "sealant" combination sold under the trademark FocalSeal® under the product designation FL8000 Material Kit by Genzyme Biosurgery, One Kendall Square, Cambridge, Mass. 02139.

Simulated Hernias

Hernias of all types are a significant part of the types of cases that can and are being done with the robot. These maladies as a whole occur in middle aged adults in the productive phase of their working lives. The benefits of a robotic inguinal hernia repair are particularly important to these active adults. Hernia repairs are one of the first surgical procedures learned in classical surgical training. A classic surgical repair in done from the "outside in" by making an incision and then exposing the defect with subsequent repair through the incision. By definition this approach requires cutting and suturing skin, subcutaneous tissue, and muscle and fascia tissue planes.

In contrast a robotic inguinal repair hernia is done from the" inside out". The robotic repair is accomplished by visualizing the defect from the inside. The peritoneal lining is elevated and the neck of the hernia sac is identified. The peritoneal out pouching or hernia sac is dissected free from the surrounding soft tissue and reduced back into the abdominal cavity. The abdominal wall defect is then covered with a mesh in order to restore the abdominal wall integrity preventing recurrent herniation of abdominal contents into a now walled off inguinal canal.

Inguinal hernia repair can be simulated by using repurposed porcine tissue. The repurposed porcine tissue includes a segment of porcine abdominal wall including all layers of the tissue. The abdominal wall is made up of essentially three layers. The innermost layer is the peritoneum. The next layer progressing outward is the muscular and fascia layer which is covered by the dermis and skin layer. The second type of porcine tissue repurposed is the porcine small bowel. A portion of small bowel is closed at one end and left open at the other end. This tissue can be used to simulate the hernia sac.

The abdominal wall can be mounted in a rectangular frame that forms an outer rim of plastic that stretches the abdominal wall tissue. An oblique incision approximately one inch in length can be made on the inner surface of the abdominal wall and carried through to the fascia layer. A downward and medial going pocket can be created in the retroperitoneal tissue. This pocket is typically made large enough to accommodate the "small bowel" hernia sac which is positioned in the pocket tracking downward and obliquely toward the midline. The closed end of the bowel is typically at the deep end of the pocket. The open end of the small bowel can then be then attached to the incision in the peritoneum, forming the opening of the hernia sac to the abdominal cavity.

The tissue frame can then be installed into a receiving receptacle fashioned in the appropriate position within the abdominal model. The abdominal model can be be modified to receive the frame so that the anatomical location of the repurposed tissue will present in an anatomically correct position.

This model can be used to facilitate teaching inguinal hernia repair by incorporating the essential steps, including port placement, and anatomically correct arm configuration to accomplish the repair within the confined space of a simulated abdomen.

The real tissue block enables an incision to be made in the peritoneum from the inside and dissection in the retroperitoneal space exposing the hernia sac, freeing of the hernia sac, and reduction of the hernia sac. Once reduced, the defect can then be covered with mesh and the mesh fixed in place from within the retroperitoneal space. The retroperitoneal incision can then be closed to complete the repair.

Representative types of hernias that can be simulated using these principles include inguinal hernia, direct hernia, indirect hernia, incisional hernias, umbilical hernias, and femoral hernias.

Other Simulated Surgeries

Non-limiting examples of other simulated surgical procedures that can be mimicked using the modified tissues, organs, and organ systems described herein include the following:

Cervicectomy, Clitoridectomy, Oophorectomy, Salpingoophorectomy, Salpingectomy, Hysterectomy, Vaginectomy, Vulvectomy, Vasectomy, Penectomy, Orchiectomy, Prostatectomy, Posthectomy, Gonadectomy, Bursectomy, Hemicorporectomy, Hemipelvectomy, Decompressive craniectomy, Hemispherectomy, Anterior temporal lobectomy, Hypophysectomy, Amygdalohippocampectomy, Laminectomy, Corpectomy, Facetectomy, Ganglionectomy, Sympathectomy/Endoscopicthoracic sympathectomy, Neurectomy, Stapedectomy, Mastoidectomy, Photorefractivekeratectomy, Trabeculectomy, Iridectomy, Vitrectomy, Gingivectomy, Glossectomy, Esophagectomy, Gastrectomy, Appendectomy, Proctocolectomy, Colectomy, Hepatectomy, Cholecystectomy, Pancreatectomy/Pancreaticoduodenectomy, Rhinectomy, Laryngectomy, Pneumonectomy, Hypophysectomy, Thyroidectomy, Parathyroidectomy, Adrenalectomy, Pinealectomy, Nephrectomy, Cystectomy, Tonsillectomy, Adenoidectomy, Thymectomy, Splenectomy, Lymphadenectomy, Adenectomy, Lumpectomy, Mastectomy, Coccygectomy, Ostectomy, Femoral head ostectomy, Astragalectomy, Discectomy, Synovectomy, Embolectomy, Endarterectomy, Frenectomy, Ganglionectomy, Lobectomy, Myomectomy, Panniculectomy, Pericardiectomy, Gastrostomy, Percutaneous endoscopic gastrostomy, Gastroduodenostomy, Gastroenterostomy, Ileostomy, Jejunostomy, Colostomy, Cholecystostomy, Hepatoportoenterostomy, Nephrostomy, Ureterostomy, Cystostomy, Suprapubic cystostomy, Urostomy, Ventriculostomy, Dacryocystorhinostomy, Amniotomy, Clitoridotomy, Hysterotomy, Hymenotomy, Episiotomy, Meatotomy, Nephrotomy, Craniotomy, Pallidotomy, Thalamotomy, Lobotomy, Bilateralcingulotomy, Cordotomy, Rhizotomy, Laminotomy, Foraminotomy, Axotomy, Vagotomy, Myringotomy, Radial keratotomy, Mini asymmetric radial keratotomy, Myotomy, Tenotomy, Fasciotomy, Escharotomy, Osteotomy, Arthrotomy, Heller myotomy, Pyloromyotomy, Analsphincterotomy, Lateral internal sphincterotomy, Sinusotomy, Cricothyrotomy, Bronchotomy, Thoracotomy, Thyrotomy, Tracheotomy, Cardiotomy, Phlebotomy, Arteriotomy, Veinotomy, and Laparotomy.

Simulated Fat Layers

In prior art simulated organ systems, a thin layer, roughly an inch or less, of simulated fat was used by preparing a layer of silicone gel/caulk over a simulated organ. While this can be representative of thin patients, it is not representative of the type of overweight to obese patients normally seen in surgical procedures.

Pig bellies tend to include a large amount of fatty tissue. This fat can be harvested, and a layer of fat up to six inches thick, but preferably between about 1 and about 4 inches in thickness, can be adhered to an organ, for example, using surgical adhesive, caulk, and the like. The surgeon cutting into a "patient" in a simulated surgical procedure using a robotic instrument will have to cut through all of this fat to get to the tissue/organ/organ system, which can provide a realistic simulation. The layer of fat can overly one or more types of tissue/organs/organ systems in the gastrointestinal tract, including stomach, duodenum, caecum, lower intestine, upper intestine, and colon, as well as the liver, gall bladder, and spleen.

Incisions can be made in an animal liver, such as a pig liver, and portions of fat inserted, to simulate a patient with fatty liver.

Simulated Tumors

In some embodiments, tumors from animals can be harvested, an incision can be made in a tissue, organ or organ system in which a simulated tumor excision is to be performed, and the tumor adhered using surgical glue or caulk, such as silicone caulk. Alternatively, caulk, such as silicone caulk, can be appropriate shaped and hardened, and be used as a simulated tumor.

Where a tissue, organ, or organ system is to include a "hidden" tumor, which is intended to be found during a simulated surgical procedure, the incision can be made anywhere it is desired, and the tumor can be located (and, ideally, exised) by the physician during the simulated surgical procedure.

Like a tumor, a placenta is also highly vascularized. When inverted, placental tissue can reasonably mimic a tumor. In some embodiments, where it is desired to simulated surgical excision of tumors, a portion of placental tissue, turned inside out, can be adhered to a desired tissue, organ, or organ system, or wrapped around an artery, vein, or spinal cord, and the surgeon can practice surgical excision of such "tumors."

Simulated Prostate Tissue

In the animal world, the pig prostate gland is not necessarily the best proxy for a human prostate gland. Although smaller in size, a dog prostate gland is fairly similar. A prostate tumor can be simulated, for example, by wrapping a dog prostate gland with a piece of inverted pig placenta, which can be adhered in place, for example, using surgical adhesive or caulk. Alternatively, tumors can be inserted through an incision in the prostate gland, and the incision can be closed with an adhesive.

Other Representative Tissues/Organs/Organ Systems

In addition to the tissues, organs, and organ systems discussed above, modified tissues, organs, and organ systems, such as hybrid or chimeric tissues, organs or organ systems, can be prepared using one or more of the following:

Human skeleton, Joints, Ligaments, Muscular system, Tendons, Mouth, Teeth, Tongue, Salivary glands, Parotid glands, Submandibular glands, Sublingual glands, Pharynx, Esophagus, Stomach, Small intestine, Duodenum, Jejunum, Ileum, Large intestine, Liver, Gallbladder, Pancreas, Nasal cavity, Pharynx, Larynx, Trachea, Bronchi, Lungs, Diaphragm, Kidneys, Ureters, Bladder, Urethra, Ovaries, Fallopian tubes, Uterus, Vagina, Vulva, Clitoris, Placenta, Testes, Epididymis, Vas deferens, Seminal vesicles, Prostate, Bulbourethral glands, Penis, Scrotum, Pituitary gland, Pineal gland, Thyroid gland, Parathyroid glands, Adrenal glands, Pancreas, Heart, Arteries, Veins, Capillaries, Lymphatic vessel, Lymph node, Bone marrow, Thymus, Spleen, Brain including Cerebral hemispheres and Diencephalon, Brain stem, including Midbrain, Pons, and Medulla oblongata, Cerebellum, Spinal cord, Ventricular system including Choroid plexus, Nerves, Cranial nerves, Spinal nerves, Eye, including Cornea, Iris, Ciliary body, Lens, and Retina, Ear including Outer ear, Earlobe, Eardrum, Middle ear, Ossicles, Inner ear, Cochlea, Vestibule of the ear, and Semicircular canals, Olfactory epithelium, Tongue, Skin, Subcutaneous tissue, and Mammary glands.

Adjusting the Osmolality of Simulated Body Fluids for Use in Electrocautery Simulations During the surgery, the osmolality of the "blood" perfusing through the tissue/organ/organ system, and the internal contents of the organs, is sufficient to allow for electrocautery to be performed.

Each of these surgeries and/or skill sets can be practiced using an appropriate tissue, organ or organ block, as discussed in detail below, where the artificial blood is perfused through the tissue, organ, or organ block during surgery, and the tissue, organ, or organ block is modified to include a proxy for the normal constituents inside the organ.

Simulated surgery involves performing an operation, whether in a traditional manner, or using robotics, on animal tissue and/or organs, and/or organ blocks including the organs, or combinations thereof. These tissues, organs, and/or organ blocks are included in simulated surgical devices, such that a surgeon can perform lifelike surgery on real, or at least realistic, tissue.

One or more of these tissue, organs, and/or organ blocks can be hooked up to a source of the artificial blood compositions described herein, and to a pump, to simulate bleeding. The organs can also include solids and/or liquids inside of them to as to simulate a realistic surgical experience.

The tissue, organs or organ blocks can be equipped with quick-connect tubes. Using these quick-connect tubes, the organs or organ blocks can be quickly incorporated into a surgical simulator, and attached to a source of "blood" to be perfused through them.

Where the organ is a colon, it can be adapted to include a fluid that is sufficiently conductive so as to permit electrocautery. This fluid can include a hydrogel, such as KY jelly, polyethylene glycol, and the like, a salt, such as sodium or potassium chloride, a color, ideally one that mirrors the color of the normal contents of the bowel, and one or more food products, such as carrots, peas, and the like. Odorants, such as butyric acid and other $C_{2-8}$ carboxylic acids acids can also be present. The same or similar components can be present in other organs in the gastrointestinal tract, although one would not necessarily expect the smell of butyric acid from a stomach, duodenum, or upper intestine.

Where surgery is to be performed on a spine, cerebrospinal fluid can be present, and leak when there is a nick in the spinal column.

Where surgery is performed on a spleen, "blood" perfusing through the spleen during the surgical procedure can leak out.

Where surgery is performed on a gall bladder, simulated bile can be present.

A review of simulated fluids that can be used can be found at Marques, et al., "Simulated Biological Fluids with Possible Application in Dissolution Testing," Dissolution Technologies, August 2015, the contents of which are hereby incorporated by reference.

Representative simulated fluids that can be applied onto and/or into the tissues, organs, or organ blocks are discussed below. These are merely representative, and other components, or other relative amounts, can be used. The goal is to simulate in a reasonable manner the types of fluids which might be found, but the pH and other factors need not be mirrored exactly.

Reagents for Preparing Simulated Body Fluid

| Reagent | Amount (g/L) |
| --- | --- |
| sodium chloride | 7.996 |
| sodium bicarbonate | 0.350 |
| potassium chloride | 0.224 |
| potassium phosphate dibasic trihydrate | 0.228 |
| magnesium chloride hexahydrate | 0.305 |

| Reagent | Amount (g/L) |
| --- | --- |
| 1M hydrochloric Acid | 40 mL |
| calcium chloride | 0.278 g |
| sodium sulfate | 0.071 |
| tris(hydroxymethyl) aminomethane | 6.057 |

Simulated Synovial Fluid

| Reagent | Amount (g/L) |
| --- | --- |
| sodium chloride | 8 |
| potassium chloride | 0.2 |
| sodium phosphate dibasic | 1.44 |
| potassium phosphate monobasic | 0.24 |
| hyaluronic acid | 3 |
| Properties - pH | 7.4 |

Simulated Gastric Fluids

| Composition | FaSSGF/ FeSSGF | Early | Middle | Late |
| --- | --- | --- | --- | --- |
| sodium taurocholate (μM) | 80 | — | — | — |
| lecithin (μM) | 20 | — | — | — |
| pepsin (mg/mL) | 0.1 | — | — | — |
| sodium chloride (mM) | 34.2 | 148 | 237.02 | 122.6 |
| acetic acid (mM) | — | — | 17.12 | — |
| sodium acetate (mM) | — | — | 29.75 | — |
| orthophosphoric acid (mM) | — | — | — | 5.5 |
| sodium diyhydrogen phosphate | — | — | — | 32 |
| milk/buffer | — | 1:0 | 1:1 | 1:3 |
| hydrochloric acid/ sodium hydroxide q.s. | pH 1.6 | pH 6.4 | pH 5 | pH 3 |
| osmolality (mOsm/kg) | 120.7 ± 2.5 | 559 | 400 | 300 |

Fasted-State Simulated Intestinal Fluid (FaSSIF)

| Composition | FaSSIF |
| --- | --- |
| sodium taurocholate (mM) | 3 |
| lecithin (mM) | 0.2 |
| maleic Acid (mM) | 19.12 |
| sodium hydroxide (mM) | 34.8 |
| sodium chloride (mM) | 68.62 |
| Properties pH | 6.5 |
| osmolality (mOsm/kg) | 180 ± 10 |
| buffer capacity (mmol/L/pH) | 10 |

Fed-State Simulated Intestinal Fluid (FeSSIF)

| Composition FeSSIF | Early | Middle | Late | FeSSIF-V2 |
| --- | --- | --- | --- | --- |
| sodium taurocholate (mM) | 10 | 7.5 | 4.5 | 10 |
| lecithin (mM) | 3 | 2 | 0.5 | 2 |
| maleic acid (mM) | 28.6 | 44 | 58.09 | 55.02 |
| sodium hydroxide (mM) | 52.5 | 65.3 | 72 | 81.65 |
| sodium chloride (mM) | 145.2 | 122.8 | 51 | 125.5 |
| glyceryl monocholate (mM) | 6.5 | 5 | 1 | 5 |
| sodium oleate (mM) | 40 | 30 | 0.8 | 0.8 |
| Properties pH | 6.5 | 5.8 | 5.4 | 5.8 |
| Osmolality (mOsm/kg) | 400 ± 10 | 390 ± 10 | 240 ± 10 | 390 ± 10 |
| buffer capacity (mmol/L/pH) | 25 | 25 | 15 | 25 |

Simulated Colonic Fluid 1 (SCoF1)

| Composition | Amount (g/L) |
|---|---|
| potassium chloride | 0.20 |
| sodium chloride | 8 |
| potassium phosphate monobasic | 0.24 |
| sodium phosphate dibasic | 1.44 |
| Properties pH | 7 |

Simulated Colonic Fluid 2 (SCoF2)

| Composition | Concentration (mM) |
|---|---|
| acetic acid | 170 |
| sodium hydroxide | ~157 |
| Properties pH | 5.8 |
| osmolality (mOsmol/kg) | 295 |
| buffer capacity (mEq/L/pH) | 29.1 |
| ionic strength | 0.16 |

A group of animal tissue collections may be made from a series of animals before butchering for food so that no animals are sacrificed beyond what would be butchered for food. By collecting a series of tissue collections by the same facility using the same procedure from the same herd of animals (same breed, same age, same food), there will be extensive similarities among the collected tissue samples.

As is understood by those of skill in art, some features vary even between identical twins such as the vascular pattern around the exterior of the heart so some features cannot be closely controlled. However, certain degrees of variability can be decreased by clustering tissue samples by gender of donor animal, nominal weight of donor animal, or some other property of the animal or classification made of the harvested tissue sample.

The organs used in the surgical simulators can be preselected so as to have various defects, such as tumors, valve defects, arterial blockages, and the like, or can be selected to be as close to identical as possible. In the former embodiment, a surgeon can demonstrate a particular type of operation where a particular defect is present, and in the latter embodiment, a surgical instructor can demonstrate a technique to multiple students, using organs that are closely matched, so that the results would be expected to be the same if the students perform the surgery correctly.

In general, the organs may be characterized using a wide variety of available metrics. These may include volume of ventricles, stiffness of the muscle tissue (restitution test), specific gravity, % fat, pressure testing, presence or absence of tumors, blockage or arteries, etc. The recorded metrics will be specific to the scenario being replicated. Ideally, the organs selected are as close to the size and weight of human organs.

Examples of classification of the tissue samples may include:
A) Some characterization of the amount of fatty material surrounding the tissue of interest.
B) Some characterization of the pliability/stiffness of the tissue.
C) Some characterization of the properties of the relevant blood vessels such as degree of occlusion.
D) One way to characterize an organ is the time it takes for a fluid to drip out from a container and into an organ. As the receiving volume of the organ will be relatively uniform (for organs of the same size) this may characterize the ability of fluids to flow through the structures in the organ and out.

Representative Xenographic Organ Preparation

Porcine organ blocks including the heart with pericardium, lungs, trachea, esophagus, and 8-12 inches of aorta can be obtained from a local supplier. There is no need to sacrifice animals to obtain these organs or organ blocks, as these can be harvested from an animal before butchering the animal for food products.

Organ preparation can begin with an incision of the pericardium on the right posterior side of the heart, so it can later be reattached with no noticeable holes when viewed from the left side. The superior vena cava, inferior vena cava, right pulmonary artery, and right pulmonary veins can then be divided with care taken to leave as much vessel length as possible. After the right lung is fully detached, the organs can be washed extensively to remove coagulated blood from the heart and vessels. All divided vessels, except for the main branch of the right pulmonary artery and right superior pulmonary vein, can be tied off, for example, using 0-silk.

As an example of quick-connect tubes, small diameter plastic tubes with Luer-Lok® connectors can then be placed into the divided right pulmonary artery and right superior pulmonary vein, and fixed in place, for example, using purse-string sutures. To create distention of the aorta, one can inject silicone caulking to the level of the ascending aorta, or, alternatively, insert a solid cylinder such as, for example, a foam backer rod.

After the silicone cures, the brachiocephalic trunk and left common carotid can be tied off, for example, using 0-silk.

The left main stem bronchus can be occluded, for example, by stapling the divided right main stem bronchus as well as the proximal trachea. The left hilum can remain unaltered, and all modifications to the heart can be hidden by the pericardium during the procedure.

Following preparation, the organs can be stored at a relatively low temperature, for example, 4 degrees Celsius, in an alcoholic solution, for example, 10% ethanol containing ½ teaspoon of red food coloring. In this manner, the organs typically remain fresh for at least 1 month. Use of higher concentrations of alcohol, such as 40% ethanol, can preserve the organs for over a year, and, ideally, up to 18 months, and can perform as well as freshly-harvested organs.

Simulating "Bleeders"

While there is value in having intact organs on which to operate, there is also value in having organs with a defect such that, during surgery, the simulation can test the surgeon's ability to handle a "bleeder."

One of the benefits of the present invention is the ability to precisely create trauma in ex vivo tissue samples, for example, by making one or more incisions, then "clotting" the blood composition to close the incision. During surgery, the clot can be dissolved, for example, by appropriately placing an agent in the blood that dissolves the clot, or by injecting an agent that dissolves the clot into an IV. The clotting agents and clot dissolving agents include those described above. The surgeon can then practice electrocautery.

Representative Endoscopic Surgical Simulator

Endoscopic procedures can be simulated, for example, using the Endoscopy VR Simulator from CAE Healthcare. This simulator is a virtual reality endoscopic simulation platform that uses realistic, procedure-based content to teach cognitive and motor skills training. It is an interactive system with tactile feedback that permits learning and practice without putting patients at risk. The tissue, while not animal tissue, looks real, and 'moves' when it is touched. The virtual patient exhibits involuntary muscle contractions, bleeding, vital sign changes, etc., and the surgeon feels feedback resistance during the simulated procedure.

Robotic Surgical Instruments

In the simulated surgical procedures described herein, one or more surgeons can perform surgery on the animal tissue, organs, and/or organ blocks using robotic surgical instruments. Typically, the robotic surgical devices include one or more arms, which control one or more tools, such as an endoscope (which provides the surgeon with the ability to see inside of the patient, and, typically, a tool selected from the group consisting of jaws, scissors, graspers, needle holders, micro-dissectors, staple appliers, tackers, suction irrigation tools, clip appliers, cutting blades, cautery probes, irrigators, catheters, suction orifices, lasers, and lights.

In robotically-assisted telesurgery, the surgeon typically operates a master controller to control the motion of surgical instruments at the surgical site from a location that may be remote from the surgical simulator (e.g., across the operating room, in a different room, or a completely different building from the surgical simulator).

The master controller usually includes one or more hand input devices, such as hand-held wrist gimbals, joysticks, exoskeletal gloves or the like. These control the movement of one or more of the robotic arms. Occasionally, line-of-sight/gaze tracking and oral commands are used to control movement of one or more of the robotic arms, and/or the audio/video components that transmit signal back to the surgeon.

For minimally invasive surgical procedures, the surgical instruments, controlled by the surgical manipulator, can be introduced into a simulated body cavity through a single surgical incision site, multiple closely spaced incision sites on the simulated body, and/or one or more natural orifices in the anatomy of the organ and/or organ block (such as through the rectum where a porcine or other animal gastrointestinal system is used as the organ block).

For some minimally invasive surgical procedures performed through particularly small entry ports, multiple surgical instruments may be introduced in a closely gathered cluster with nearly parallel instrument shafts.

A more detailed explanation of certain the components of robotic systems is provided below:

A robotic surgical system includes a master system, also referred to as a master or surgeon's console, for inputting a surgical procedure and a slave system, also referred to as a patient-side manipulator (PSM), for robotically moving surgical instruments at a surgical site within a patient. The robotic surgical system is used to perform minimally invasive robotic surgery. One example of a robotic surgical system architecture that can be used to implement the systems and techniques described in this disclosure is a da Vinci®. Surgical System manufactured by Intuitive Surgical, Inc. of Sunnyvale, Calif. Alternatively, a smaller scale robotic surgical system with a single manipulator arm may be suitable for some procedures. The robotic surgical system also includes an image capture system, which includes an image capture device, such as an endoscope, and related image processing hardware and software. The robotic surgical system also includes a control system that is operatively linked to sensors, motors, actuators, and other components of the master system and the slave system and to the image capture system.

The system is used by a system operator, generally a surgeon, who performs a minimally invasive simulated surgical procedure on a simulated patient. The system operator sees images, captured by the image capture system, presented for viewing at the master system. In response to the surgeon's input commands, the control system effects servo-mechanical movement of surgical instruments coupled to the robotic slave system.

The control system includes at least one processor and typically a plurality of processors for effecting control between the master system, the slave system, and the image capture system. The control system also includes software programming instructions to implement some or all of the methods described herein. The control system can include a number of data processing circuits (e.g., on the master system and/or on the slave system), with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein. In one embodiment, control system may support wireless communication protocols such as Bluetooth, IrDA, HomeRF, IEEE 802.11, DECT, and Wireless Telemetry.

The robotic surgical system can also include an instrument chassis that couples to the slave system. The instrument chassis provides a common platform for coupling surgical instruments and endoscope for introduction into an entry point on the simulated patient. In one embodiment, the entry point can be a mouth, where access to the throat or larynx is desired, the rectum where access to the gastrointestinal system, or, more particularly, to the colon, is desired, or previously-prepared or surgically created openings or orifices.

In one embodiment, the system can also include an instrument chassis having a proximal section and a distal section. The chassis supports an endoscope. Generally, the dimensions and shape of the chassis at its distal section are typically reduced compared to its proximal end, to minimize the volume of the surgical equipment near the surgical entry point. Instrument interfaces can be movably mounted to the proximal section of the instrument chassis. Surgical instruments can be mounted at the proximal end to the instrument interface. Surgical instruments can be mounted at its proximal end to the instrument interface. The interface drives movable components in the surgical instrument as described in U.S. Pat. No. 6,491,701 which is incorporated by reference herein, in its entirety. The interface drives the instrument in a similar way. The surgical instruments are also movably coupled to the distal section of the chassis. The instrument interfaces are mounted to the proximal section of the chassis such that rotational and linear motion is permitted. Specifically, an instrument interface mounting or a flexible instrument shaft permits a pitch motion of the instrument interfaces relative to the chassis, a yaw motion of the instrument interfaces relative to the chassis and an insertion sliding motion of the instrument interfaces relative to the chassis. The system can function in a manner similar to the manner in which chopsticks operate, in that small motions at the proximal end of the tool, near a pivot location, can correspond to larger motions at the distal end of the tool for manipulating objects.

An actuation system operates the components of instrument, such as an end effector and various wrist joints. An actuation system operates the components of instrument, such as an end effector and various wrist joints. The actuation systems can include motors, actuators, drive systems, control systems, and other components for effecting controlling the instruments. An interface actuation system controls the movement of the instrument with respect to the chassis, and an interface actuation system controls the movement of the instrument with respect to the chassis. The surgical system can be configured to manipulate one, two, or more instruments.

Some robotic surgery systems use a surgical instrument coupled to a robotic manipulator arm and to an insertion linkage system that constrained motion of the surgical instrument about a remote center of motion aligned along the shaft of the surgical instrument and coincident with a patient entry point, such as an entry incision. Further details of these methods and systems are described in U.S. Pat. Nos. 5,817,084 and 6,441,577, which are incorporated by reference herein in their entirety.

Actuators can be operably coupled to interface discs. A more detailed description of the interface discs and their function in driving a predetermined motion in an attached surgical instrument is fully described, for example, in U.S. Pat. No. 7,963,913, filed Dec. 10, 2006, disclosing "Instrument Interface of Robotic Surgical System," which is incorporated by reference herein in its entirety.

Various embodiments of surgical instruments, end effectors, and wrist mechanisms are explained in detail in U.S. Pat. Nos. 5,792,135; 6,331,181; and 6,817,974, which are incorporated by reference herein in their entirety.

Switching from Robotic Surgery to Manual Surgery

One drawback of using robotic surgery is that instruments may need to be quickly removed when there is a "bleeder." Conventional surgical techniques may be required to find the source of the bleed, and close the bleed, before the rest of the surgical procedure can be performed. This can be difficult to practice, as it can be difficult to pre-program when a bleed will occur.

In one aspect of the invention, one or more of the tissues, organs, or organ blocks described herein includes a clot formed using animal blood, human blood, or the artificial blood compositions described herein and a clotting agent. The clot is dissolved during the simulated surgical procedure when the blood compositions, which, in this embodiment, contain an anti-clotting agent, are in sufficient contact with the clot to dissolve the clot. In another aspect of the invention, an anti-clotting agent is introduced, for example, into an IV bag, to cause the clot to dissolve.

When the clot dissolves, the surgeon using a robotic surgical apparatus either has to fix the resulting "bleeder" using the robotic surgical apparatus, or remove the apparatus from the patient, and go in manually to fix the bleeder.

Accordingly, in this embodiment, the simulated surgical systems can provide a more realistic experience than those in which there is never the possibility of having a bleeder.

VI. Kits

In another embodiment, the invention described herein relates to kits for use in simulated surgical procedures. In one aspect of this embodiment, the kits include the artificial blood compositions and one or more of the modified animal tissues, organs, or organ blocks, which can be, for example, from pigs.

In one aspect of this embodiment, the tissue, organs, or organ blocks include a clot, formed by cutting the tissue, organs, or organ blocks, and forming a clot using either blood or the blood composition described herein, and a clotting agent. The kits can further include an anti-clotting agent, such as an amylase or protease, to dissolve the clot and start the flow of blood through the cut.

In another aspect of this embodiment, the kits include a blood composition as described herein, which includes an anti-clotting agent, and tissue, organs, or organ blocks which include a clot.

In another aspect of this embodiment, the kits include a blood composition as described herein, and an anti-clotting agent.

The present invention will be better understood with reference to the following non-limiting examples:

Example 1: Preparation of a Modified Porcine Bowel

As an example of a type of animal organ that can be modified for use in simulated surgical procedures that involve electrocautery, a porcine bowel was modified using the techniques outlined below.

Objective

Prepare a wedge of small bowel complete with the supporting mesentery, lymph nodes and vasculature including the mesenteric artery and portal vein which support the chosen segment of small bowel.

Anatomy

The porcine small bowel is supplied with arterial blood via a vessel named the mesenteric artery. It is located in the root of the mesentery and is a branch of the aorta. The vessel is largest at its proximal or aortic end and slowly tapers until it nearly disappears at the cecum. The artery is closely adherent to the portal veins. The portal vein drains blood from the bowel and carries it back to the liver. The portal vein is very thin walled. It is smallest at the cecal end of the small bowel and progressively becomes larger as it progresses toward the liver. The flow in the portal vein increases as it approaches the liver because it collects flow from blood vessels entering it from the mesentery. The artery on the other hand has progressively less blood flow as it gives off side branches and flow as it makes its way down the mesentery. The artery is deep to the portal vein and dorsal to the vein. The vascular bundle is surrounded by lymph nodes.

The mesenteric artery gives off multiple small vessels which coarse up to the bowel via perpendicular vessels which are arrayed sequentially within the mesentery. The perpendicular vascular bundle contains veins which are in close proximity to the arteries and lymphatic vessel. The perpendicular veins drain blood from the bowel back into the venous plexus from which the blood drains into the portal vein and ultimately the liver. The venous plexus is a compact aggregation of interconnected venous structures that form a spongy highly vascular band like network of veins that are at the base of the mesentery dorsal to the artery and vein. The vasculature including the venous plexus are within the root of the mesentery and surrounded on both the dorsal and ventral side by multiple lymph nodes which sandwich the vascular structures.

Dissection Method

The preparation of the small bowel segment is begun by choosing a segment of small bowel that is subtended by an intact lymph node bearing mesenteric root. The perpendicular vessels are visualized after the bowel is positioned flat. A point is chosen between two perpendicular vessels near the junction of the perpendicular vessels and the venous plexus. A second similar spot is chosen at a spot one-inch lateral to the initial spot. This is chosen in order to capture and isolate in the intervening tissue enough arterial feeder vessels to perfuse the selected small bowel segment. This portion of mesenteric tissue describes an area in the dissection known as the neck of the wedge of tissue to be prepared.

The perpendicular vessels between these two spots will be the vessels that contain the arterial vessels and the draining venous vessels which vascularize the segment of bowel of interest.

Two additional spots ½ inch lateral to the first two spots are chosen at the mesenteric junction between the perpendicular vessels and the venous plexus. The perpendicular vessels extending upward from this segment of the root of the mesentery to the bowel are ligated. These vessels are vessels that extend to and drain bowel that will be removed from the specimen. These spots will mark the lateral aspects of portion of mesenteric root that will be included in the wedge of tissue prepared for use in the simulation. The venous plexus is cut perpendicular to its main axis toward the root of the mesentery from this most lateral spot dividing the lymph node bundle as well as the underlying portal vein and mesenteric artery. By dividing the venous plexus at this point the perpendicular vessels that supply the wedge tissue are protected from compression or damage when the venous plexus is ligated. The location of the transection enables the portal vein and the mesenteric artery supplying the segment of interest to be controlled without compromising the vasculature of the segment of small bowel of interest. These cuts once the lymph node and vascular structures have been divided are then angled to meet one another to form the point of the wedge at the base of the mesentery.

The plane between the lymph nodes and the underlying vasculature is opened and the lymph node bundles are reflected off of the underlying vessels and venous plexus back to the margin of the neck of the wedge of small bowel exposing the vasculature so that the venous plexus and the artery and vein can be safely managed. The venous plexus is then ligated at both ends to prevent bleeding. Ligation of the venous plexus is accomplished lateral to the neck of the segment in order to obviate compromise of the neck vasculature. The largest and most proximal arterial orifice is cannulated with a catheter which is secured in place in order to perfuse the bowel segment. Both ends of the portal vein are then sutured closed. The opposite end of the artery is sutured closed.

The mesentery between the perpendicular veins from the mesenteric root upward to the bowel beginning at the initial spots that delineate the neck of the segment is then divided. The bowel is then divided perpendicular to its longitudinal axis. This frees the wedge segment of small bowel.

Figure 2A:
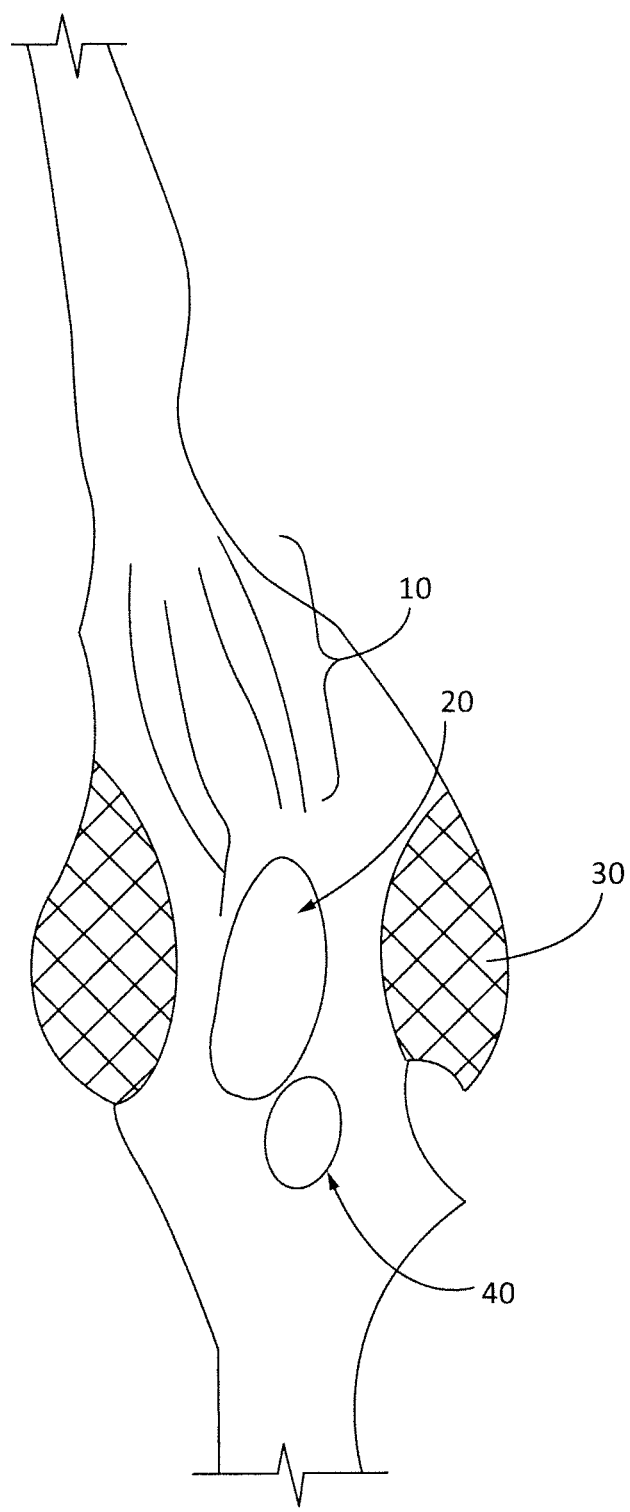
FIG. 2A is a photograph showing the small bowel anatomy when the root is cut perpendicular to the axis of blood flow.
Figure 2B:
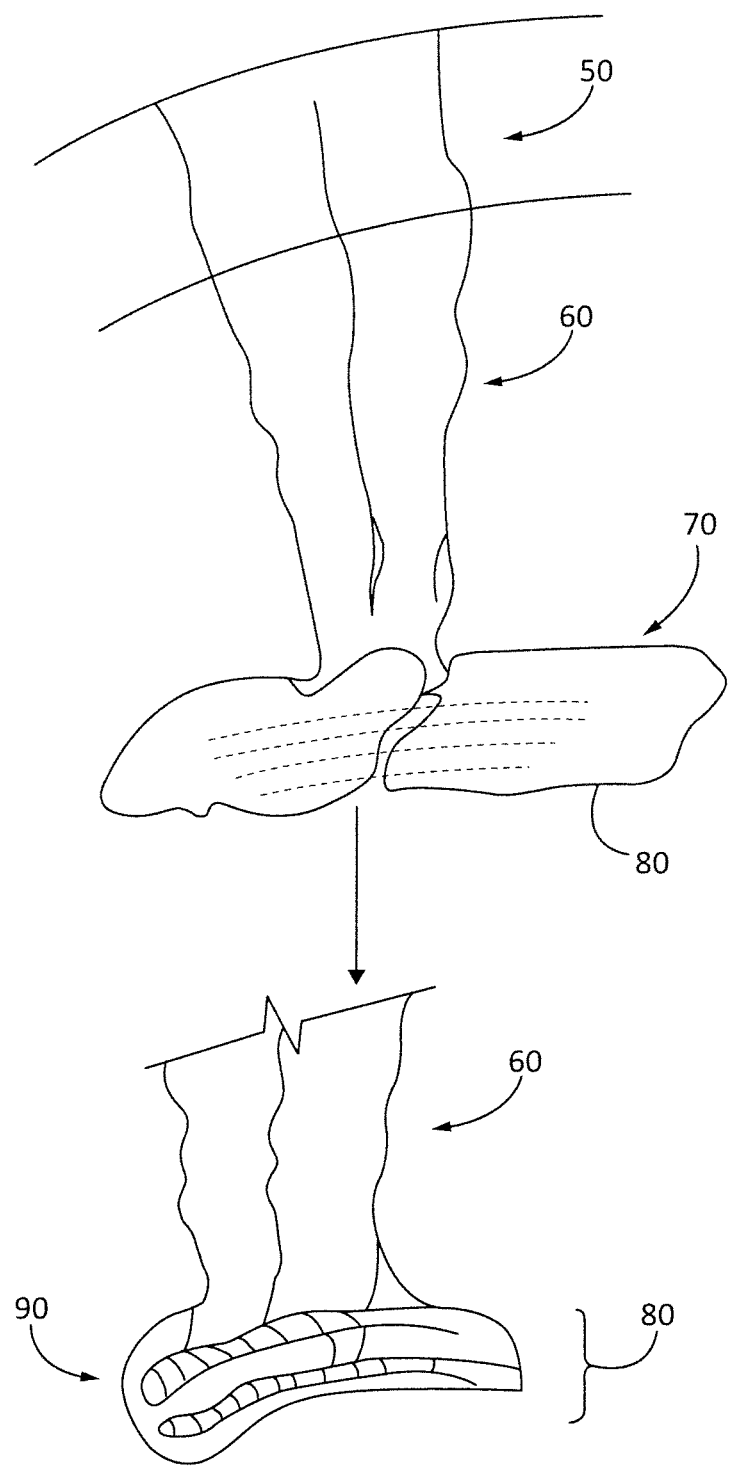
FIG. 2B is a schematic illustration of the location of lymph nodes and vessels in relation to the bowel.
Figure 3:
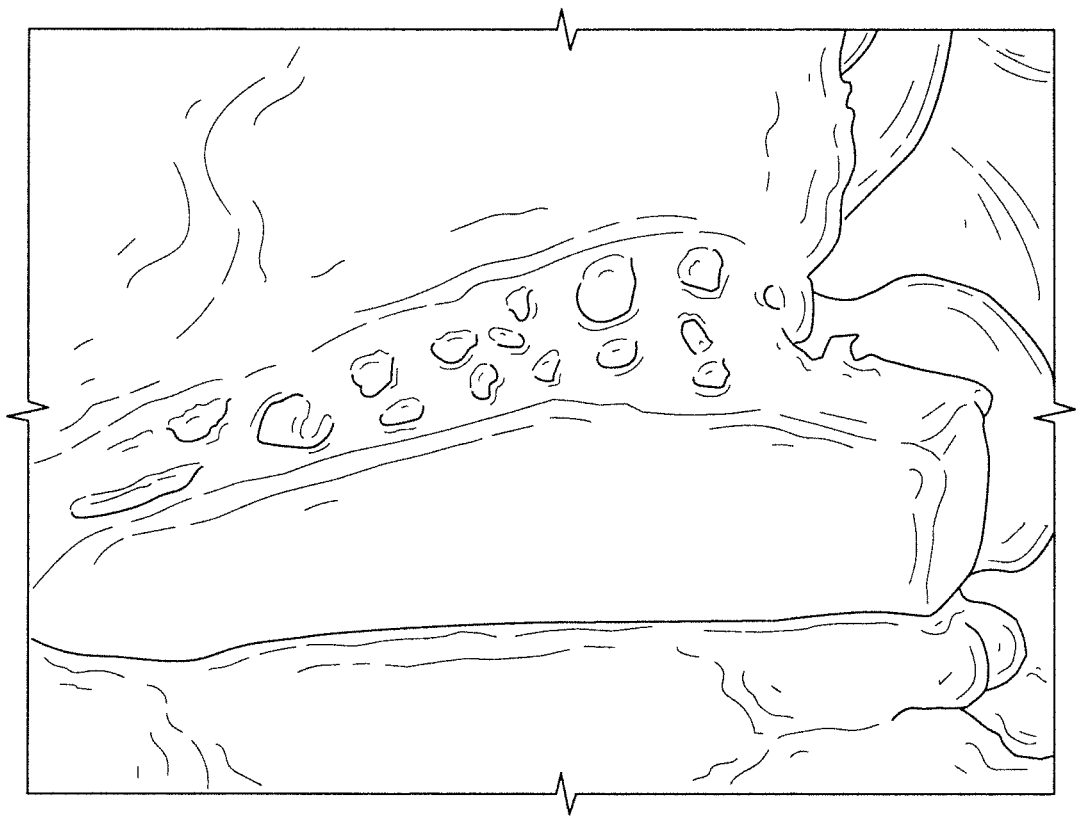
FIG. 3 shows the mesenteric artery and portal vein opened longitudinally, showing the orifices and vessels which emanate from the artery, and which empty into the portal vein.
Figure 4:
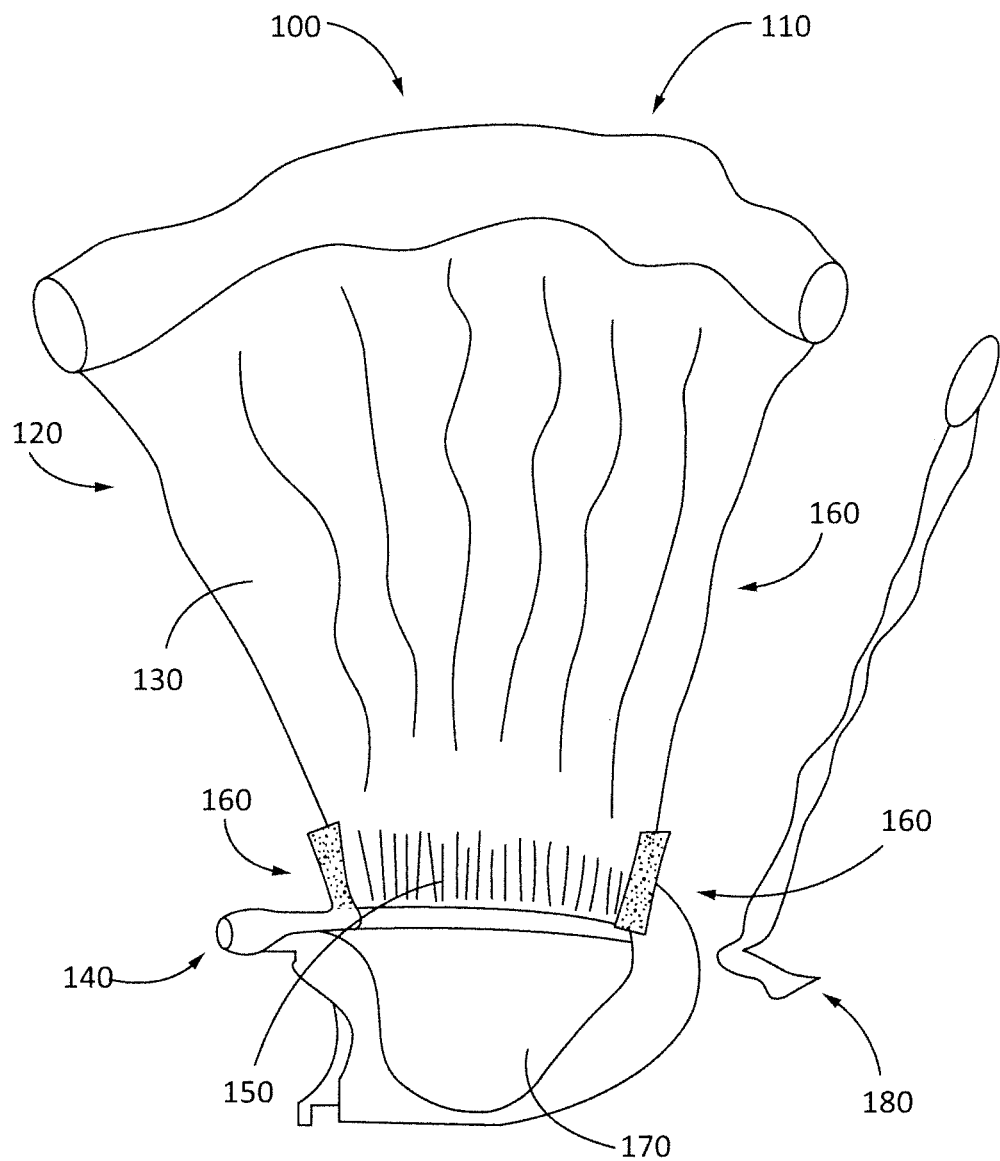
FIG. 4 is a drawing which shows the preparation of a small bowel wedge.

The dissection and preparation method described above is shown in FIGS. 1, 2A, 2B, 3 and 4. FIG. 1 is a photograph showing a porcine small bowel, including the mesenteric lymph nodes, perpendicular vessel and small bowel. FIG. 2A shows the small bowel anatomy when the root is cut perpendicular to the axis of blood flow. 10 represents the plexus, 20 represents the vein, 30 represents the nodes, and 40 represents the artery. FIG. 2B is a schematic illustration of the location of lymph nodes and vessels in relation to the bowel. 50 represents the bowel, 60 represents perpendicular vessels, 70 represents lymph nodes, 80 represents arcade vessels, and 90 represents areas where lymph nodes have been removed. FIG. 3 shows the mesenteric artery and portal vein opened longitudinally, showing the orifices and vessels which emanate from the artery, and which empty into the portal vein. FIG. 4 is a drawing which shows the preparation of a small bowel wedge. 100 represents a wedge, 110 represents the bowel, 120 represents bile, 130 represents mesentery, 140 represents vein cannulus, 150 represents venous plexus, 160 shows where cauterization takes place, 170 represents a tongue of tissue, and 180 represents the manges.

Using the technique outlined above, the bowel is attached to a source of fake blood, which can perfuse through the bowel during a simulated surgical procedure. The fake blood described herein ideally has a sufficient salt concentration that it can conduct electricity sufficiently well to permit electrocautery to be performed.

All references referred to herein are hereby incorporated by reference for all purposes.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

The invention claimed is:

1. A tissue block for simulated surgery, comprising:
   isolated animal tissues harvested from more than one animal;
   one or more of an adhesive and fastener adhering together the isolated animal tissues into at least one simulated human organ for simulated surgery; and
   a salt-containing hydrogel formulation contained within the at least one simulated human organ, said salt-containing hydrogel formulation having salt in an amount sufficient for electrocautery, said salt-containing hydrogel formulation adding viscosity to the at least one simulated human organ.

2. The tissue block of claim 1, wherein the at least one simulated human organ is filled or partially filled with the salt-containing hydrogel formulation, and wherein partially filled is defined as between about 10 and about 99 percent of the volume of the simulated human organ.

3. The tissue block of claim 1, wherein the hydrogel formulation comprises KY jelly or polyethylene glycol.

4. The tissue block of claim 1, wherein the at least one simulated human organ comprises an organ in the gastrointestinal tract.

5. The tissue block of claim 1, wherein the at least one simulated human organ is perfused with a source of fake blood, wherein the fake blood has an osmolality between about 220 and about 400 milliosmoles per kilogram.

6. The tissue block of claim 5, wherein the fake blood has a pH between about 6.4 and about 8.4.

7. The tissue block of claim 5, wherein the fake blood comprises one or more colorants, salts and/or buffers.

8. The tissue block of claim 1, wherein the at least one simulated human organ comprises an animal placenta, turned inside out.

9. The tissue block of claim 1, wherein the at least one simulated human organ comprises one or more simulated tumors or animal tumors inserted into or adhered to the at least one simulated human organ, or wherein the at least one simulated human organ is modified to include one or more blood clots, bleeders, or vascular occlusions.

10. A tissue block for simulated surgery, comprising:
    isolated animal tissues harvested from more than one animal, the isolated animal tissues comprising porcine tissue;
    one or more of an adhesive and fastener adhering together the isolated animal tissues into at least one simulated human organ for simulated surgery;
    a salt-containing hydrogel formulation contained within the at least one simulated human organ, said salt-containing hydrogel formulation having salt in an amount sufficient for electrocautery, said salt-containing hydrogel formulation adding viscosity to the at least one simulated human organ; and a source of fake blood to perfuse the at least one simulate human organ, the fake blood having an osmolality between about 220 and about 400 milliosmoles per kilogram.

11. The tissue block of claim 10, wherein the at least one simulated human organ is filled or partially filled with the salt-containing hydrogel formulation, wherein partially filled is defined as between about 10 and about 99 percent of the volume of the simulated human organ.

12. The tissue block of claim 10, wherein the hydrogel formulation comprises KY jelly or polyethylene glycol.

13. The tissue block of claim 10, wherein the at least one simulated human organ comprises an organ in the gastrointestinal tract.

14. The tissue block of claim 10, wherein the fake blood has a pH between about 6.4 and about 8.4.

15. The tissue block of claim 10, wherein the fake blood comprises one or more colorants, salts and/or buffers.

16. A method for making a tissue block for simulated surgery, the method comprising:

adhering together isolated animal tissues into at least one simulated human organ for simulated surgery, the isolated animal tissues harvested from more than one animal; and providing a salt-containing hydrogel formulation contained within the at least one simulated human organ, said salt-containing hydrogel formulation having salt in an amount sufficient for electrocautery, said salt-containing hydrogel formulation adding viscosity to the at least one simulated human organ.

17. The method of claim 16, comprising filling or partially filling the at least one simulated human organ with the salt-containing hydrogel formulation, and wherein partially filled is defined as between about 10 and about 99 percent of the volume of the simulated human organ.

18. The method of claim 16, wherein the hydrogel formulation comprises KY jelly or polyethylene glycol.

19. The method of claim 16, wherein the at least one simulated human organ comprises an organ in the gastrointestinal tract.

20. The method of claim 16, comprising perfusing the at least one simulated human organ with a source of fake blood, wherein the fake blood has an osmolality between about 220 and about 400 milliosmoles per kilogram.

21. The method of claim 20, wherein the fake blood has a pH between about 6.4 and about 8.4.

22. The method of claim 20, wherein the fake blood comprises one or more colorants, salts and/or buffers.

23. The method of claim 16, further comprising a layer of pig fat adhered to or inserted into the at least one simulated human organ.

* * * * *